United States Patent [19]

Bishop

[11] Patent Number: 5,401,535
[45] Date of Patent: Mar. 28, 1995

[54] PRECIOUS METAL COMPOSITION

[75] Inventor: Peter T. Bishop, Reading, United Kingdom

[73] Assignee: Johnson Matthey Public Limited Company, London, United Kingdom

[21] Appl. No.: 155,827

[22] Filed: Nov. 23, 1993

Related U.S. Application Data

[62] Division of Ser. No. 875,412, Apr. 29, 1992, Pat. No. 5,281,635.

[30] Foreign Application Priority Data

May 17, 1991 [GB] United Kingdom ............... 9110757
Jul. 19, 1991 [GB] United Kingdom ............... 9115621

[51] Int. Cl.$^6$ .............................................. B05D 3/02
[52] U.S. Cl. .................................. 427/229; 427/377; 427/385.5
[58] Field of Search ................. 427/229, 377, 385.5

[56] References Cited

U.S. PATENT DOCUMENTS

| | | | |
|---|---|---|---|
| 1,207,284 | 12/1916 | Feldt et al. | 556/113 |
| 2,370,593 | 2/1945 | Trenner et al. | 556/113 |
| 2,490,399 | 12/1949 | Ballard | 556/113 |
| 2,490,717 | 12/1949 | Steiger | 556/113 |
| 2,509,198 | 5/1950 | Moore | 556/113 |
| 2,660,549 | 12/1953 | Friedheim | 556/113 |
| 2,994,614 | 8/1961 | Fitch | 556/113 |
| 3,018,191 | 1/1962 | Caban et al. | 427/376.7 |
| 3,163,665 | 12/1964 | Fitch | 106/1.26 |
| 3,245,809 | 4/1966 | Fitch | 106/1.26 |
| 3,391,010 | 7/1968 | Hauel | 427/229 |
| 3,438,748 | 4/1969 | Hippoliet | 556/113 |
| 4,780,502 | 10/1988 | Lotze et al. | 524/104 |

FOREIGN PATENT DOCUMENTS

| | | |
|---|---|---|
| 491147 | 6/1992 | European Pat. Off. . |
| 392656 | 3/1924 | Germany . |
| 1533628 | 11/1978 | United Kingdom . |
| 2047672 | 12/1980 | United Kingdom . |
| 1603472 | 11/1981 | United Kingdom . |
| 2097811 | 11/1982 | United Kingdom . |
| 2154248 | 9/1985 | United Kingdom . |
| 2216536 | 10/1989 | United Kingdom . |

OTHER PUBLICATIONS

Karen Brown et al., J. Am. Chem. Soc. vol. 103, No. 16, 1981, 4943–4945 (no mo.).
Donald Brown et al: J. Chem. Soc. Dalton Trans. (3) 199–201 (1978) (no mo.).
A K Al-S'asy et al., Inorganic Synthesis, vol. 23, 191 (1985) "A General Synthesis for Gold(I) Complexes", Unusual Ligands and Compounds (no mo.).
Chemical Abstracts, N053999504 o. 99291n–vol. 106, No. 13, 1986, Columbus, Ohio, and "Journal of Inorganic Biochemistry" vol. 28, No. 2–3, London, pp. 253–261.

*Primary Examiner*—Janyce Bell
*Attorney, Agent, or Firm*—Stevens, Davis, Miller & Mosher

[57] ABSTRACT

A homogeneous composition for forming on firing a film of precious metal, which is one or more of platinum, palladium, gold and silver, on a substrate, for instance to decorate table ware, comprises polymeric resin and a solution, in water and a co-solvent, of thiolate of the precious metal, the composition containing 3–22% by weight of the precious metal as the thiolate, and the co-solvent, resin and thiolate being such that as the composition on a substrate dries and is progressively heated in firing, the water evaporates off to leave a homogeneous composition of the resin and thiolate in the co-solvent, then the co-solvent evaporates off to leave a homogeneous composition of the thiolate in the resin, and then the thiolate decomposes to the precious metal while the resin volatilize.

18 Claims, No Drawings

PRECIOUS METAL COMPOSITION

This is a division of application Ser. No. 07/875,412, filed Apr. 29, 1992, U.S. Pat. No. 5,281,635.

This invention relates to a composition for forming a film of precious metal on firing the composition, and to a method of forming a film of precious metal on a substrate using the composition.

Compositions which form a film of precious metal (by which is meant in this specification one or more of platinum, palladium, gold and silver) on firing are useful particularly for decorating ceramic or glass substrates.

Commercially available liquids for this purpose are based on organic solvents and are complex mixtures containing (a) a precious metal compound which decomposes on firing to form the precious metal, (b) metal compounds, such as those of rhodium, bismuth or chromium, to improve the colour, adhesion or brightness of the fired film and (c) resin and organic solvent to dissolve or carry (a) and (b).

It would be desirable to reduce or eliminate such organic solvent so as to reduce or eliminate any environmental hazards it presents, for instance in the preparation, transportation or use of compositions containing it, for example from the fumes released on applying the compositions or firing them. Such a task is not straightforward, however, because the compositions still of course need to be stable, apply readily and produce good films on firing. A composition which is based on water rather than on organic solvent would have the added advantage that materials, such as brushes or screen printing screens or stencils, with which the composition came into contact could be cleaned with water-based cleaning agents. In spite of these advantages, there is no water-based bright gold composition commercially available as far as we know. A water-based composition has now been invented.

UK patent specification 2097811A discloses a paint medium for applying overglaze decoration to pottery, characterised in that it comprises:
- 15-40% by weight of polyvinyl pyrrolidone or a mixture of polyvinyl pyrrolidone and aqueous polyethylene oxide,
- 45-85% by weight of ethylene glycol and/or propylene glycol, and optionally water.

The specification mentions colouring matter which may be oxides and gold and organic gold compounds.

UK specification 2216536A discloses a burnish gold composition containing 10-40% by weight of gold in the form of gold powder and/or a sparingly soluble gold compound, 2-20% by weight of polyvinyl pyrrolidone, 3-30% by weight of an aqueous acrylate resin dispersion with 30-60% by weight of solids content, and 5-50% by weight of water.

The present invention provides a homogeneous composition for forming on firing a film of precious metal, which is one or more of platinum, palladium, gold and silver, on a substrate, which composition comprises polymeric resin and a solution, in water and a co-solvent, of thiolate of the precious metal, the composition containing 3-22% by weight of the precious metal as, the thiolate, and the co-solvent, resin and thiolate being such that as the composition on a substrate dries and is progressively heated in firing, the water evaporates off to leave a homogeneous composition of the resin and thiolate in the co-solvent, then the co-solvent evaporates off to leave a homogeneous composition of the thiolate in the resin, and then the thiolate decomposes to the precious metal while the resin volatilises.

The invention provides also a method of forming a film of precious metal on a substrate, which method comprises applying the composition to a substrate and drying and firing the applied composition.

The invention also provides a transfer bearing the composition which has been dried thereon.

Some of the present thiolates are novel compounds, and the invention provides novel compounds as such, in particular a thiolate which is a gold compound of formula AuSR" or a salt thereof, in which R" is such that HSR" represents:
- 4,6-dihydroxy-2-mercaptopyrimidine; or
- N-(mercaptoalkanoyl)glycine whose alkane group contains 1 or 2 carbon atoms.

The invention provides also a process for preparing a novel thiolate, which process comprises reacting in a solvent a compound of formula AuCl(SR'$_2$) with a thiol of formula HSR" to form the gold compound, and in solution, the sulphide of formula SR'$_2$.

The invention provides also a process for preparing a novel thiolate, which process comprises reacting a tetrahaloaurate with a thiol of formula HSR" to form the gold compound.

The invention also provides a process for preparing a novel thiolate, which process comprises reacting a thiol of formula HSR" with a gold(I) amine complex of formula

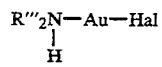

wherein Hal represents a halogen atom and each R''' is the same or different and represents an aliphatic, aromatic or heterocyclic group or the two R'''' symbols together with the N atom represent a cyclic amine to form the gold compound.

Though the present composition still contains co-solvent, the composition is water-based. It can be diluted with water (i.e., it is water-thinable) and need not contain as much organic solvent as conventional liquid precious metal formulations. It can be applied readily, and produces good films on firing.

It is surprising that a water-soluble (not colloidal) precious metal compound can be employed. The invention is based on the discovery that this can be done if the compound is a dissolved thiolate and, as the composition is progressively heated on firing, the precious metal compound remains in homogeneous composition, preferably in solution, until the precious metal compound decomposes to the precious metal while its carrier matrix volatilises.

For clarity, the invention is described in terms of heating to leave a homogeneous composition, preferably a solution, of the precious metal thiolate in the co-solvent and then a homogeneous composition, preferably a solution, of the thiolate in the resin. It will be recognised, however, that the thiolate may change in structure during the heating; what is important, however, is that whatever the form of the subsequent precious metal compound, it remains in homogeneous composition, preferably in solution. Similarly, the resin may decompose during its volatilisation.

As the present composition is heated, a homogeneous composition is maintained, so that the thiolate does not precipitate until it decomposes to the precious metal while the resin volatilises. The thiolate is in solution in the initial composition, and it is preferred that it remain in solution during the heating until it decomposes to the precious metal while the resin volatilises. Accordingly, it is preferred that the composition comprises a solution, in water and a co-solvent, of polymeric resin and thiolate of the precious metal, the composition containing 3-22% by weight of the precious metal as the thiolate, and the co-solvent, resin and thiolate being such that as the composition on a substrate dries and is progressively heated in firing, the water evaporates off to leave a solution of the resin and thiolate in the co-solvent, then the co-solvent evaporates off to leave a solution of the thiolate in the resin, and then the thiolate decomposes to the precious metal while the resin volatilises.

The present composition usually contains 5-85% of water. Percentages herein are by weight. The composition can be diluted with water for application. The composition contains preferably 15-70%, especially 40-55%, of water. It is especially advantageous that the composition contain a greater weight of water than the total of all organic solvent.

The precious metal usually comprises gold or platinum, especially gold. Specific instances are:
(a) gold;
(b) platinum;
(c) gold and platinum;
(d) gold and palladium;
(e) gold and platinum and palladium; and
(f) any one of (a)-(e) and silver.

Preferably, the precious metal is (a), (b), (d) or any one of these and silver.

A thiol is an organic compound which is an analogue of an alcohol, the oxygen atom of the hydroxyl group of the alcohol having been replaced formally by a sulphur atom. A metal thiolate is a derivative of a thiol in which the hydrogen atom of its SH group is replaced formally by a metal atom. The present precious metal thiolate must form a solution in the water/co-solvent mixture, and also be such as to fulfill the other functions demanded. Usually the thiolate employed has a solubility in water at 20° C. of at least 100, preferably 200-300, grams per litre. Preferably, the thiolate, usually in the form of a salt, is soluble in the water alone. Advantageously, the precious metal, especially gold, thiolate starts to decompose to precious metal above 200° C.; such thiolates tend to give bright rather than dull films after firing. Suitable thiolates are known compounds.

The thiolate can be an aliphatic, aromatic or heterocyclic thiolate, preferably containing at least one group selected from nitro groups and groups of formula —COOH, —SO$_2$OH, —OH, —CO.NH$_2$, —NH$_2$ or —O—P(O)(OH)$_2$, any of whose H atoms optionally being substituted, or a salt thereof. Such thiolates are discussed below with reference to the precious metal being gold. Thus, a preferred group of thiolates are gold compounds of formula:

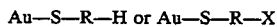

Au—S—R—H or Au—S—R—X or a salt of either, in which:
X represents a nitro group or a group of formula —COOH, —SO$_2$OH, —OH, —CO.NH$_2$, —NH$_2$ or —O—P(O)(OH)$_2$, any of whose hydrogen atoms optionally being substituted; and
R represents a divalent organic group.

Although the gold compounds are described, in the conventional way, as being of a mononuclear formula such as Au—S—R—X, it will be understood that in fact they may be of polynuclear formula to satisfy the 2-coordinate nature of gold(I) complexes.

Any substituent in X is usually an aliphatic, aromatic or heterocyclic group or an optionally substituted amino group, for instance an amino group mono- or di-substituted by alkyl of 1-6 carbon atoms. The aliphatic group is usually alkyl of 1-6 carbon atoms, for instance ethyl, isopropyl or n-butyl. The aromatic group is usually optionally substituted phenyl, any substituent usually being X as here defined, alkyl of 1-6 carbon atoms or mercapto whose hydrogen atom is optionally substituted by a gold atom. The heterocyclic group is usually optionally substituted purine, pyridine or pyrimidine, any substituent usually being X as here defined, alkyl of 1-6 carbon atoms, or an aromatic group as described above. The —CO.NH$_2$ or —NH$_2$ group may be mono- or di-substituted, for instance by alkyl of 1-6 carbon atoms optionally substituted by X as here defined.

When R represents a divalent aliphatic group (i.e. the group attached to S is aliphatic rather than aromatic or heterocyclic), it is usually a divalent hydrocarbon of 1-7 carbon atoms (e.g. alkane of 1-6 carbon atoms or toluene) optionally substituted by X as defined above, usually by one X, or by an oxo group on a non-terminal carbon atom. When R represents a divalent aromatic group (i.e. the group attached to S is aromatic rather than aliphatic or heterocyclic), it is usually divalent benzene optionally substituted by X as defined above, usually by one X. When R represents a divalent heterocyclic group (i.e. the group attached to S is heterocyclic rather than aliphatic or aromatic), it is usually divalent pyrimidine, purine or pyridine optionally substituted by X as defined above (usually by one X) and/or by phenyl (usually by no more than one phenyl) and/or by alkyl of 1-6 carbon atoms (usually by no more than one such alkyl group).

X preferably represents —COOH.

In a particular embodiment, —R—X represents —CH$_2$CH$_2$X, —CH(CH$_3$)CO.NH.CH$_2$X, —CH$_2$CH$_2$CO.NH.CH$_2$X, —CH$_2$C$_6$H$_4$—p—X, —CH$_2$COCH$_2$CH$_2$X, —CH(X)CH$_2$X, —CH$_2$CH(NH$_2$)X, —CH$_2$CO.NH.CHX.CH$_2$.C$_3$H$_3$N$_2$, —CH$_2$CO.NH.CH$_2$CH$_2$CO.NH.CHX.CH$_2$.C$_3$H$_3$N$_2$, —CH$_2$CONH.CH$_2$CH$_2$CO.NH.CH$_2$CO.NH—CH$_2$X, —CH$_2$CH(CO.NH.CH$_2$X)NH-.CO.CH$_2$CH$_2$CH(NH$_2$)X or —CS.N(CH$_3$)CH$_2$CH$_2$X, in which X represents —COOH, C$_6$H$_4$ represents divalent benzene and C$_3$H$_3$N$_2$ represents imidazol-4-yl.

In another particular embodiment, —R—X represents —CH$_2$CH$_2$X or —CH$_2$—C$_6$H$_4$—p—X, in which X represents a nitro group or a group of formula —SO$_2$OH, —OH or —NH$_2$ and C$_6$H$_4$ represents divalent benzene.

In a further particular embodiment, —R—X represents —C$_6$H$_4$—p—X, in which X represents a nitro group or a group of formula —SO$_2$OH, OH or NH$_2$ and C$_6$H$_4$ represents divalent benzene.

In a yet further particular embodiment of the gold compounds of formula Au—S—R—H—or Au—S—R—X, H—S—R—H or H—S—R—X represents:
4,5-diamino-6-mercapto-2-phenylpyrimidine,
2-amino-6-mercapto-8-methylpurine,
2mercapto-4-amino-pyridopyrimidine,
2-mercaptopyridine,
2-mercaptobenzoxazole,
2-mercaptobenzimidazole, 5-mercapto-1-methyltetrazole,
4-mercaptopyridine,
2-mercapto-5-nitrobenzimidazole, or
4-amino-6-hydroxy-2-mercaptopyrimidine.

The sulphur atom which links to the gold atom in a preferred class of gold compounds is linked to the same carbon atom, or is separated by one carbon atom from the carbon atom, which bears a substituted amido group, so that these compounds contain the group

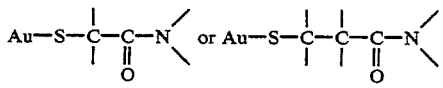

Specific examples of this class are gold compounds of formula Au—S—R—H or Au—S—R—X which are such that H—S—R—H or H—S—R—X represents:
N-(2-mercaptopropionyl)glycine,
N-(3-mercaptopropionyl)glycine,
N-(2-mercaptoacetyl)glycine,
2-mercaptoacetyl-L-histidine or
2-mercaptopropionyl-L-histidine.

Another preferred class of gold compounds is of formula:

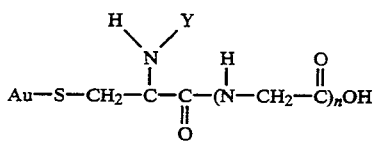

in which n represents O or an integer of at least 1 and Y represents a hydrogen atom or an alkanoyl group of 2-6 carbon atoms which may optionally bear a single amino(carboxy)methyl group. The amino(carboxy)methyl group, when present, is usually on the terminal carbon atom of the alkanoyl group. Usually n represents O or an integer of 1-.

Specific examples of this class are gold compounds of formula Au—S—R—H or Au—S—R—X which are such that H—S—R—H or H—S—R—X represents:
acetylcysteine,
glutathione or
L-cysteine.

A specific preferred gold thiolate is N-(2-mercaptopropionyl)glycine gold (I), of formula:

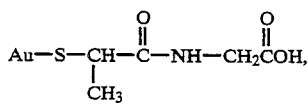

which may alternatively be written in the Zwitterion form:

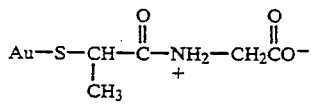

though the thiolate is believed to be polynuclear in accordance with the discussion above.

With regard to this gold thiolate, we refer to UK patent specification 2047672A. The reference is not concerned with film formation, but with preparing a $^{195\,m}$Au-containing liquid by adsorbing $^{195\,m}$Hg onto a certain adsorption agent and then eluting the daughter radioisotope $^{195\,m}$Au. Table I on page 5 lists combinations of adsorption agents and eluants, and among these eluants is an aqueous solution of mercaptopropionyl glycine. There is no specific disclosure of the use of this eluent, and no specific data on the present gold thiolate. Example II describes a series of experiments in which certain liquids containing $^{198}$Au. are passed through certain adsorption agents. The Example explains that the isotope $^{198}$Au was employed instead of the daughter radioisotope $^{195}$Au because inter alia of the short half-life of $^{195\,m}$Au . The Example states that the liquids were prepared by dissolving 1-3 μg of gold containing $^{198}$Au in 1 ml of an aqueous solution having a pH of about 5-6 and containing 0.001-0.1 molar of one of a Table of what it calls gold ion complexing agents. One of the agents is mercaptopropionyl glycine, and the Table records that employing it with the adsorption agent SiO$_2$/Ag left 88% of the $^{198}$Au not adsorbed. We believe that employing mercaptopropionyl glycine as the agent would not give the present gold thiolate, but gold having moieties strongly adsorbed on the surface of the metal, and hence not having one gold atom per N-(2mercapto-propionyl)glycine ligand as the present gold thiolate does. In any event, the gold materials suggested or disclosed in this reference are radioactive. They would decay to become progressively less radioactive, but some radioactivity would remain. The gold in the present gold thiolates is preferably naturally occurring gold, which is non-radioactive. Thus, it is preferred that the gold in the present N-(2-mercaptopropionyl)glycine gold(I) or salt thereof be non-radioactive (and hence is not a mixture of the non-radioactive form with the radioactive form). It is preferred that all the present thiolates, not only N-(2-mercaptopropionyl)glycine gold(I) or a salt thereof, be non-radioactive.

The optionally substituted sulpho group (—SO$_2$OH) which X can represent in the present gold thiolates introduces more sulphur, which generally forms sulphur oxides on firing the composition to form a film, and hence it is less preferred that X has this value. Nitro and optionally substituted hydroxyl groups tend to make the thiolate less water-soluble and less stable to reduction than is ideal, and hence it is less preferred that X has either of these values. Generally, it is most preferred that X represents optionally substituted carboxy.

The thiolate can be in the form of a salt. Salts can be formed with bases by reason for instance of the carboxy or sulpho group which X can represent. A thiolate which forms a salt with a base can be employed in basic solution which forms the salt therein. Any salt is preferably with ammonia or an organic base particularly an optionally substituted amine, any substituent being for instance alkyl of 1-6 carbon atoms optionally substituted by X as defined above. Particular optionally substituted amines of interest are triethylamine, ethanolamine, diethanolamine, triethanolamine, pyridine, morpholine or diisopropylamine, especially the first four of these.

Where the present thiolates are novel, they can be made in ways known in themselves. Where the thiolate is a salt, it can be made for instance by reaction with a base.

When the present thiolate is a gold compound of formula AuSR'' or a salt thereof in which R'' is such that HSR'' represents N-(mercaptoalkanoyl)glycine whose alkane group contains 1 or 2 carbon atoms, it can be seen that the N-(mercaptoalkanoyl)glycine is:
N-(2-mercaptoacetyl)glycine, N-(3-mercaptopropionyl)glycine, or
N-(2-mercaptopropionyl)glycine.
The last mentioned is particularly outstanding.

The present thiolates can be prepared by the general procedure of A K Al-Sa'ady et al, Inorganic Synthesis, volume 23, 191(1985), represented in the case of gold by the general equations:

$$[AuCl_4]^- + 2SR'_2 \rightarrow [AuCl(SR'_2)] + R'_2SO + 2HCl + Cl^-$$

$$[AuCl(SR'_2)] + HSR'' \rightarrow AuSR'' + HCl + SR'_2$$

Au(III) in the form of tetrachloroaurate anion is reduced to Au(I) by a water-soluble sulphide of formula $SR'_2$. Each R' radical is the same or different and preferably represents methyl, ethyl or 2-hydroxyethyl. Preferably the water-soluble sulphide is ethyl 2-hydroxyethyl sulphide. Addition of the appropriate thiol ligand via the thiol HSR'', usually at ambient temperatures, yields a gold thiolate, generally as a white precipitate though in the case of mercaptosuccinic acid as a yellow solution. The reaction solvent is usually water, ethanol or isopropanol, preferably water so that soluble inorganic salts (for example NaCl) can be extracted by water-washing. Yields of the gold thiolates can be as high as 80% or more (based on gold), with the remainder soluble in water. The gold thiolates produced can be dissolved in water by the addition of a base, usually an organic base, for instance an optionally substituted amine, to form the corresponding salt, in this instance a substituted ammonium salt.

The present gold thiolates can also be prepared by reacting a tetrahaloaurate (particularly a tetrachloroaurate or tetrabromoaurate) with the thiol of formula HSR'' to form the gold compound.

The present gold thiolates can also be prepared by reacting the thiol of formula HSR'' with a gold(I) amine complex of formula

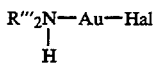

wherein Hal represents a halogen atom (preferably a chlorine or bromine atom) and each R''' is the same or different and represents an aliphatic, aromatic or heterocyclic group, or preferably the two R''' symbols together with the N atom represent a cyclic amine (such as benzotriazole or pyridine) to form the gold compound. The aliphatic, aromatic or heterocyclic groups which R''' may represent can be such groups as are discussed above as substituents in X.

The present thiolate can be formed in situ in the present composition, for instance by forming a salt therein, for example as described above.

The present composition contains 3-22% of precious metal, as the thiolate. The composition preferably contains 8-12% of the precious metal, especially gold, as the thiolate. The composition usually contains 10-40%, preferably 14-26%, of the thiolate, especially gold thiolate.

The polymeric resin must form a homogeneous composition with the other ingredients, and also be such as to fulfil the other functions demanded. The resin preferably forms a solution in the water/co-solvent mixture, though it may form a dispersion or emulsion therein. Preferably, the resin is soluble or forms a clear dispersion, in the water alone. Suitable resins are known materials. Polyacrylic, polymethacrylic, polyvinyl pyrrolidone, polycellulose ether, polyamide, polyethylene glycol, polyester, polyacrylamide, polyvinyl acetate, polyvinyl alcohol, alkyd, polyamine or polyurethane, resins or mixtures thereof can be employed. The resin can be in the form of a co-polymer or graft polymer. The resin can contain solubilising groups, particularly carboxylate and/or hydroxy and/or amino groups, especially carboxylate groups, to enhance the water solubility of the resin. Preferably, the resin comprises one or more, usually one, of polyvinyl pyrrolidone resins, polymethacrylic resins and polycellulose ether resins, for instance one or more, usually one, of polymethacrylic resins and polycellulose ether resins. Resins tend to volatilise steadily over a range of temperatures rather than all the substance volatilising at the same temperature. Preferably, the present resin is chosen such that the majority at least of it volatilises in the range 200°-550° C. Preferably, the resin comprises polyvinyl pyrrolidone, polymethacrylic or polycellulose ether resin the majority of which volatilises in this range.

The resin must satisfy the present requirements that on firing, the thiolate forms a homogeneous composition, preferably a solution, in it, and then the thiolate decomposes to the precious metal while the resin volatilises. For instance, if gold mercaptosuccinic acid, which decomposes to gold around 150° C., is employed in a composition analogous to the present compositions but whose resin starts to evaporate around 200°-300° C., then on firing, a homogeneous composition (for instance a solution) of the thiolate in the resin is not formed. Instead, a premature dispersion of gold in the resin forms. A dull film results. However, the same resin can be employed successfully to produce bright gold films with a thiolate with which it does satisfy these requirements; and the same thiolate can be employed successfully to produce bright gold films with a resin with which it does satisfy these requirements. For example, N-(2-mercaptopropionyl)glycine gold(I) starts to decompose around 200° C. and decomposes to gold around 280°-300° C.; it can be employed successfully to produce bright gold films with resins which volatilise around 280°-300° C. and which would be unsuccessful with gold mercaptosuccinic acid.

The present composition can contain less than 5 % of the resin but usually contains 5-45%, especially 7-13%, of the resin. The weight ratio of resin solid to precious metal, especially gold, in the thiolate can be for instance at least 1:1, e.g. at least 1.2:1, for instance at least 1.5:1, as these tend to produce better, "scum-free", and brighter films on firing. Satisfactory bright films have been obtained, however, using ratios from 0.1:1 to 1.5:1. A typical composition has a ratio of 1:1.

The co-solvent must, with the water, dissolve the precious metal thiolate and form a homogeneous composition, preferably a solution, with the resin, and be such as to fulfil the other functions demanded. The co-solvent is preferably of boiling point between 100° and 280° C., for instance between 100° and 220° C. A preferred group of co-solvents are the water-miscible alcohols, ethers or esters, especially the water-miscible alcohols. Preferably, the co-solvent comprises 1,2-propanediol, 1,3-propanediol, n-butanol, tetrahydrofuran acetate, glycerol, glycerol diacetate or ethyl lactate, especially 1,2-propanediol, 1,3-propanediol or ethyl lactate. The particular co-solvent can affect the brightness of the films on firing.

The composition usually contains 5–45%, preferably 15–30%, for instance 25–30%, of the co-solvent.

It will be appreciated that particular ingredients and their amounts depend on each other and that any candidate material can readily be tested. For instance, it has been found that when the resin is a cellulosic resin the content of the co-solvent in the composition. is preferably 25–30%, while when the resin is an acrylic or methacrylic resin the content of the co-solvent in the composition is preferably 15–30%.

The composition can contain minor metal compound additives, such as compounds of palladium (for example palladium sulphate), rhodium, bismuth or chromium, generally used in combination, to improve the colour, adhesion or brightness of the fired film, particularly on pottery. Minor metal compound additives for the film particularly on glass can be for instance compounds of silver. vanadium or silicon. For bright films, the additives are usually in solution in the composition. They may be present, for instance, in a total content of 0.01–5%, usually 0.1–0.4%, of the composition. Such additives and their amounts and function are known in themselves for use in conventional liquid precious metal compositions based on organic solvents.

Known minor metal additive compounds which are soluble in the present mixture of water and co-solvent can be employed, for example chromium trioxide or $[Cr_2(SO_4)_3]$; ammonium bismuth citrate or bismuth lactate; $[RhCl(ox)(NH_3)]$, $[Rh(gly)_3]$, $[Rh_2(acetate)_4]9$, $Na_3[Rh(NO_3)_6]$ or $[Rh(acac)CO]$; $Me_3SiOMe$; or $[VO(acac)_2]$; wherein acac represents acetylacetonate, ox oxolate and gly glycinato. In a particular embodiment, the rhodium, bismuth or silver is employed as the same thiolate as is the precious metal, for instance Ag N-(2-mercapto-propionyl)glycine. Thus, where the thiolate of the precious metal is a gold compound of formula Au—S—R—X or a salt thereof, the rhodium minor metal additive can be of formula $[Rh(SRX)_3]$.

The composition must be homogeneous, for ease of application etc. To improve the rheology of the composition for application and to control the drying of the applied film, the composition can contain additional solvent, such as a water-miscible alcohol for instance isopropanol or n-hexanol, a water-miscible ketone for instance butanone, or a water-miscible solid for instance 1,6-hexandiol. The content of additional solvent is preferably 5–10% of the composition. The composition can contain surfactant, for instance in a content of 0.05–0.5%, for example to improve the brushing properties of the composition.

A particular composition according to the invention consists essentially of:

| | |
|---|---|
| Polyvinyl pyrrolidone | 7–13% |
| Gold thiolate | 14–26% |
| 1,2-propanediol | 15–30% |
| Water | 40–55% |
| Isopropanol | 5–10% |
| Minor metal additives | 0.1–0.4% |

A preferred composition according to the invention consists essentially of:

| | |
|---|---|
| Polyvinyl pyrrolidone | 7–13% |
| Gold thiolate | 14–26% |
| 1,2-propanediol | 15–30% |
| Ethyl lactate | 15–30% |
| Water | 30–55% |

| -continued | |
|---|---|
| Isopropanol | 5–10% |
| Minor metal additives | 0.1–0.4% |

The present composition may be UV-curable by reason of the polymeric resin being UV-curable, or may be cured thermally by reason of the polymeric resin being thermosetting.

The present composition can be applied to substrates and fired, each in ways known in themselves and this is advantageous as conventional equipment and techniques can be employed. The substrate on which firing occurs is preferably ceramic, such as porcelain or china, or glass. The composition can be applied directly to the substrate. Alternatively, the composition can be applied in the desired pattern (for instance, a decorative pattern) to a transfer substrate and dried thereon to form a transfer; the transfer can then be used in the usual way to transfer the pattern to the substrate, such as a ceramic substrate, on which it is fired. The composition can be applied for instance by brushing, by using a steel wheel or neoprene wheel or by printing, for example ink jet printing (otherwise known as inject or injection printing) but preferably screen printing. Particular components in the composition suit particular application procedures and the particular composition employed depends on the particular application procedure, bearing in mind for instance the desired theology. The applied composition is usually dried, for instance at ambient temperature, before firing. It can, however, be dried as part of the heating sequence for firing. The present compositions are usually fired at 200°–900° C., for instance 460°–650° C. on a glass substrate, 650°–900° C. on a ceramic substrate, and 200°–350° C. on a plastic substrate.

The present composition produces good films. Precious metal films fall into three classes, burnished, self-burnished and bright. Compositions for forming burnished films, which—as the name implies—need to be burnished to produce the desired film, contain precious metal powder, or in some cases, insoluble precious metal compound. The fired films usually contain a greater weight of precious metal than do those of bright films but are dull in appearance, exhibiting no significant reflectivity. After firing, they are burnished by mechanical abrasion, for instance with sand and water, to give a matt appearance. More recently, self-burnished films have been introduced. These contain insoluble matting agent which gives the fired film the appearance and durability of a burnished film without the necessity of burnishing. Compositions for forming bright films contain soluble precious metal compound. The fired films are very reflective, often having "mirror-like" properties. The present composition can be of any of these types. Preferably, it produces a bright film on firing. The composition can contain in addition, however, precious metal powder or insoluble precious metal compound to produce a burnished film on firing and then burnishing. Alternatively, the present composition can contain in addition an insoluble matting agent to produce a self-burnished film on firing.

The present composition is preferably used to decorate the substrate, for instance to produce decorative table ware. The composition can be used, however, for electronic applications, for instance to lay down electrically conductive pathways on insulating materials.

The invention is illustrated by the following Examples, in which the rhodium complex unless otherwise stated is of formula Rh(acac)CO wherein acac represents the acetylacetonate group, the polycellulose ether resin is "Natrasol" resin supplied by Aqualon Limited, United Kingdom, the polymethacrylic resin is "Versicol K11" supplied by Allied Colloids, Bradford, United Kingdom, the polyvinyl pyrrolidone is supplied by Aldrich Chemicals, United Kingdom and the compositions used for film formation unless otherwise indicated are all solutions. Unless otherwise stated, these compositions were brushed onto glazed china and then heated to a maximum of 780° C. during a one hour firing cycle, with a ten minute soak at maximum temperature.

Example 1

N-(2-mercaptopropionyl)glycine gold(I) was prepared in a two-necked 1000 ml round-bottomed flask as follows:

A solution of sodium tetrachloroaurate (35g) in distilled water (200 ml) was slowly added to a solution of ethyl 2-hydroxyethyl sulphide (20.5 g) in distilled water (200 ml). Solid addition of mercaptopropionylglycine (5.21 g) followed by vigorous stirring yielded gold mercaptopropionylglycine as a white solid (yield, based on gold, 85%).

Analysis: Theory: C, 16.8 N, 3.9
Found: C, 16.15 N, 3.65 %
Melting Point=230° C. (with decomposition).

Comparative Examples 1-3

In an analogous way to Example 1, there were prepared:
gold L-cysteine;
gold 2-mercaptoethanesulphonic acid; and
gold 2-mercaptopyridine;
each in a yield, based on gold, in excess of 80%.

Comparative Example 4

Gold mercaptosuccinic acid was produced in an analogous way to Example 1 except that isopropanol was used instead of water and that the gold complex was soluble in the isopropanol and hence was isolated by evaporation of the solvent under reduced pressure (0.1 Torr) and then trituration of the resulting oil with diethyl ether to produce a white precipitate (yield, based on gold, in excess of 80%).

Comparative Example 5

In an analogous way to Example 1, there was prepared:
gold 4-hydroxythiophenol (Analysis for C: Theory 22.3% Found 21.8%)
in a yield, based on gold, in excess of 80%.

Example 2

In an analogous way to Example 1, there was prepared:
gold 4,6-dihydroxy-2-mercaptopyrimidine; (Analysis for C: Theory 13.9% Found 13.2 %)
in a yield, based on gold, in excess of 80%.

Comparative Example 6

The following composition was obtained by mixing the ingredients:

|  | Parts |
| --- | --- |
| Polycellulose ether resin | 10 |
| Bis(ethylenediamine)gold trichloride | 22 (10.1 parts gold) |
| 1,3-Propanediol | 15 |
| Water | 38 |
| Isopropanol | 15 |
| Rhodium complex | 0.05 |
| Chromium trioxide | 0.05 |

In these Examples, parts are by weight and the resin contents are based on their dry weights.

The composition was brushed onto china and heated to a maximum of 780° C. for 10 minutes during a one hour firing cycle. A dull and pitted film resulted. The film was not adherent; gentle rubbing removed it.

It can be seen that the gold compound is not the present gold thiolate.

Comparative Example 7

The following composition was prepared and used in an analogous way to Comparative Example 6:

|  | Parts |
| --- | --- |
| Polymethacrylic resin | 11 |
| Gold mercaptosuccinic acid | 18 (11 parts gold) |
| 1,3-Propanediol | 15 |
| Water | 40 |
| Isopropanol | 15 |
| Rhodium complex | 0.05 |
| Chromium trioxide | 0.05 |

A dull, adherent, film resulted. The dull nature of the film was due to premature decomposition of the thiolate during firing to give an insoluble gold product.

Comparative Examples 8-10

Compositions were prepared and used in an analogous way to Comparative Example 7 by substituting for its gold thiolate the following gold thiolate, in an amount corresponding to 10 parts of gold:
Gold cysteine (Comparative Example 8)
Gold mercaptobenzoic acid (Comparative Example 9)
Gold 2-mercaptopyridine (Comparative Example 10)

In each case, a dull film resulted. The dull nature of the film was due to premature decomposition of the thiolate during firing to give an insoluble gold product. The film was not adherent; gentle rubbing removed it.

Comparative Example 11

The following composition was prepared and used in an analogous way to Comparative Example 6:

|  | Parts |
| --- | --- |
| Polycellulose ether resin | 17 |
| Gold thiobarbituric acid | 17 (10 parts gold) |
| 1,3-Propanediol | 15 |
| Ethyl lactate | 15 |
| Water | 20 |
| Isopropanol | 15 |
| Triethylamine | 1 |
| Rhodium complex | 0.05 |
| Chromium trioxide | 0.05 |

A dull and pitted film resulted. The dull nature of the film was due to premature decomposition of the thiolate during firing to give an insoluble gold product. The film was not adherent; gentle rubbing removed it.

Example 3

The following composition was prepared and used in an analogous way to Comparative Example 6:

|  | Parts |
| --- | --- |
| Polymethacrylic resin | 10 |
| N-(2-mercaptopropionyl)glycine gold(I) | 18.5 (10 parts gold) |
| 1,3-Propanediol | 15 |
| Water | 40 |
| Isopropanol | 15 |
| Triethylamine | 1 |
| Rhodium complex | 0.05 |
| Chromium trioxide | 0.05 |

A bright, adherent, film resulted.

It can be seen that the composition contains 10% gold as the thiolate.

The composition was also was also applied by steel wheel and by neoprene wheel. In both cases, it gave the same result as the brushing.

Examples 4–6

Example 3 was followed except that for its 1,3-propanediol there were substituted 15 parts of tetrahydrofuran acetate (Example 4), glycerol diacetate (Example 5) or ethyl lactate (Example 6). In each case, the resulting gold film was adherent and essentially bright.

The composition was applied also by steel wheel, and also neoprene wheel. In each case, a bright, continuous film was obtained on firing.

Examples 7–9

The following compositions were prepared and used in an analogous way to Comparative Example 6:

Example 7

|  | Parts |
| --- | --- |
| Polycellulose ether resin | 10 |
| N-(2-mercaptopropionyl)glycine gold(I) | 18.5 (10 parts gold) |
| 1,2-Propanediol | 15 |
| Ethyl lactate | 15 |
| Water | 40 |
| Triethylamine | 1 |
| Rhodium complex | 0.05 |
| Chromium trioxide | 0.05 |

Example 8

|  | Parts |
| --- | --- |
| Polyvinyl pyrrolidone resin (molecular weight 30,000) | 12 |
| N-(2-mercaptopropionyl)glycine gold(I) | 16.5 (9 parts gold) |
| 1,2-Propanediol | 15 |
| Ethyl lactate | 25 |
| Water | 30 |
| Triethylamine | 1 |
| Rhodium complex | 0.05 |
| Chromium trioxide | 0.05 |
| Ammonium bismuth citrate | 0.05 |

Example 9

|  | Parts |
| --- | --- |
| Polyethylene glycol resin (molecular weight 20,000) | 10 |
| N-(2-mercaptopropionyl)glycine gold(I) | 18.5 (10 parts gold) |
| 1,2-Propanediol | 15 |
| Glycerol | 5 |
| Ethyl lactate | 10 |
| Water | 40 |
| Rhodium complex | 0.05 |
| Chromium trioxide | 0.05 |

In each case, a bright, adherent film resulted.

Comparative Example 12

The following composition was obtained and used in an analogous way to that of Comparative Example 6:

|  | Parts |
| --- | --- |
| Polyvinyl pyrrolidone | 91 |
| Gold-2-mercaptobenzimidazole | 182 |
| Water | 273 |
| 1,2-Propanediol | 91 |
| Ethyl lactate | 227.5 |
| Ammonia solution (specific gravity 0.88) | 45.5 |
| [Rh$_2$ (acetate)$_4$] | 1 |
|  | 811 |

A dull non-adherent film resulted from the firing of the composition. This was a result of the low solubility of the gold compound during application (brushing) of the composition, resulting in a heterogeneous composition on heating. It was estimated that only about 5% of the gold-mercaptide was dissolved in the initial medium.

Comparative Examples 13–19

Compositions were prepared and used as in Comparative Example 12 by substituting for its gold compound the following:

13. Gold-5-mercapto-1-methyltetrazole
14. Gold-2-mercapto-5-nitrobenzimidazole
15. Gold-4-aminothiophenol
16. Gold-4-hydroxythiophenol
17. Gold-mercaptoacetic acid
18. Gold-2-mercaptopropionic acid
19. Gold-mercapto-2,3-hydroxypropane.

The resultant films were all unsatisfactory. The compositions of Comparative Examples 13–15 were unsatisfactory for the same reason as that of Comparative Example 12, resulting in dull and particulate films, often with severe pitting. The compositions of Comparative Examples 16–19 prematurely decomposed to gold powder during the production or use of the liquid gold compositions, resulting in heterogeneous compositions. The gold compounds of Comparative Examples 16–19 and their general classes are inherently unstable in the presence of organic base and therefore are not useful for producing bright gold films from water based media.

Example 10

A water-based liquid gold composition that has a resin solid to gold ratio of 1:10 was prepared by mixing:

|  | Parts |
| --- | --- |
| Polycellulose resin | 9.1 |
| ("Natrasol 250GR" sold by Aqualon, UK) | |
| N-(2-mercaptopropionyl)glycine gold(I) | 182 |
| Water | 273 |
| 1,2-propanediol | 91 |
| Ethyl lactate | 182 |
| Triethylamine | 45.5 |
| [$Rh_2$(acetate)$_4$] | 1 |
|  | 783.6 |

It can be seen that the composition contains 1.2% of the resin by weight.

The resulting film was bright and continuous, after gently washing off with water the low amount of inorganic deposit left on the film and then drying with tissue paper.

Example 11

A composition was prepared and used as in Example 10 by substituting for its gold compound gold-acetylcysteine. It gave the same result.

Example 12

A water-based liquid gold composition containing gold-(γ-L-glutamyl-L-cysteinyl-glycine), otherwise called gold-glutathione, was prepared by mixing:

|  | Parts |
| --- | --- |
| Polyvinyl pyrrolidone | 72 |
| Gold-glutathione | 172 |
| Water | 290 |
| 1,2-propanediol | 72 |
| Ethyl lactate | 91 |
| Triethylamine | 68 |
| [$Rh_2$(acetate)$_4$] | 1 |
|  | 766 |

The resulting film was bright and continuous.

Example 13

A water-based liquid gold composition containing gold and palladium to produce a metallic (grey) fired appearance was prepared by

|  | Parts |
| --- | --- |
| Polyvinyl pyrrolidone | 50 |
| N-(2-mercaptopropionyl)glycine gold(I) | 100 |
| Palladium sulphate | 15 |
| Water | 150 |
| 1,2-prepanediol | 50 |
| Ethyl lactate | 100 |
| Triethylamine | 25 |
| Polysulphide solution | 12.5 |
| [RhCl(ox)($NH_3$)$_4$] | 1 |
|  | 503.5 |

0x=oxalato; polysulphide solution=a 15% ammonium polysulphide solution in water (obtained from BDH, United Kingdom). The resulting film was bright and continuous in appearance.

Example 14

A water-based liquid gold composition suitable for fast and slow firing cycles was prepared by mixing:

|  | Parts |
| --- | --- |
| Polyvinyl pyrrolidone | 30 |
| N-(2-mercaptopropionyl)glycine gold(I) | 100 |
| Water | 240 |
| 1,2-propanediol | 30 |
| Ethyl lactate | 125 |
| n-Butanol | 5 |
| Triethylamine | 25 |
| Polysulphide solution | 12.5 |
| [RhCl(ox)($NH_3$)$_4$] | 1 |
| $Cr_2(SO_4)_4$ | 1.9 |
| [Bi-citrate] | 2.5 |
|  | 572.9 | ox=oxalate; Bi-citrate was purchased from BDH, United Kingdom, as ammonium bismuth citrate. The polysulphide solution was as in Example 13. Reflective and continuous films were obtained from the following firing profiles:

Fast firing: 40 minute cycle; maximum temperature=805° C.; 2 minutes soak.

Slow firing: 200° C. per hour; maximum temperature=750° C.; 10 minutes soak.

The same composition was brushed onto porcelain ware to produce a bright and continuous film using the same firing cycle as Comparative Example 6. The same composition brushed onto porcelain ware was fired to a maximum temperature of 900° C.; 40 minute cycle; 2 minutes soak, to produce a bright and continuous film.

Example 15

A water-based liquid gold composition suitable for application to glassware was prepared by mixing:

|  | Parts |
| --- | --- |
| Polymethacrylic resin | 100 |
| ("Versicol K11" from Allied Colloids, UK) | |
| N-(2-mercaptopropionyl)glycine gold(I) | 200 |
| Water | 380 |
| 1,3-propandiol | 20 |
| 2-propanol | 100 |
| [Rh(CO)(acac)]$_2$ | 2 |
| $CrO_3$ | 1 |
| $Me_3SiOMe$ | 1 |
| Silver-N-(2-mercaptopropionyl)glycine | 30 |
|  | 734 |

The composition was brushed onto glassware, and fired for one hour in total to a maximum temperature of 620° C., 10 minutes soak. A bright and continuous film resulted.

Example 16

A water-based liquid gold composition suitable for ink-jet printing and having a high water concentration was prepared by mixing:

|  | Parts |
| --- | --- |
| Polyvinyl pyrrolidone | 74 |
| N-(2-mercaptopropionyl)glycine gold(I) | 59 |
| Water | 314.4 |
| Butanone | 46 |
| n-Butanol | 39 |
| Triethylamine | 8 |
| Polysulphide solution | 10 |
| [Rh($NH_3$)$_6$]$Cl_3$ | 1 |
| [Bi-lactate] | 1.4 |

| | Parts |
|---|---|
| | 614.4 |

The composition of Example 16 contains 61% water. The polyvinyl pyrrolidone resin has a molecular weight=10,000 daultons. The polysulphide solution is as in Example 13. The composition was sprayed by an ink-jet sprayer onto flat tiles and fired to produce a bright and continuous gold film.

Example 17

A water-based liquid gold composition that is suitable for screen-printing was prepared by mixing:

| | Parts |
|---|---|
| Polycellulose resin | 45 |
| N-(2-mercaptopropionyl)glycine gold(I) | 181 |
| Water | 454 |
| 1,2-propanediol | 181 |
| Glycerol | 91 |
| Ethyl lactate | 45 |
| [Rh$_2$(acetate)$_4$] | 1 |
| [Cr$_2$(SO$_4$)$_2$] | 1.8 |
| | 999.8 |

The composition contains 4.5% resin as solid. The composition was printed through a screen of mesh size 305μ onto glazed tile. The fired film was bright and continuous. A low amount of inorganic deposit left on the film after firing was gently washed with water and then dried with tissue paper, to give a bright and continuous film.

Example 18

A water-based liquid gold composition which contains gold powder to produce a burnished effect, and which is suitable for screenprinting was prepared by mixing:

| | Parts |
|---|---|
| Polycellulose resin | 62 |
| Gold powder | 400 |
| N-(2-mercaptopropionyl)glycine gold(I) | 250 |
| Water | 1000 |
| 1,2-propanediol | 250 |
| Ethyl lactate | 62 |
| Glycerol | 125 |
| Triethylamine | 62 |
| [Rh$_2$(acetate)$_4$] | 1 |
| | 2212 |

The composition was applied in an analogous way to that of Example 17. The resulting film was abraided to produce an off-bright gold effect.

Example 19

In the same way as described for the composition of Example 19, a brushing burnish gold was prepared by simply reducing the polycellulose resin concentration to 25 parts.

Example 20

In an analogous way to Example 1, there was prepared gold-N-(3-mercaptopropionyl)glycine in a yield, based on gold, in excess of
Analysis: Theory: C, 16.8 N, 3.9

Found: C, 16.35 N, 3.55 %

I claim

1. A method of forming a film of precious metal which is one or more of platinum, palladium, gold and silver on a substrate, which method comprises applying a homogeneous composition to a substrate and drying and firing the applied composition, said composition comprising polymeric resin and a solution, in water and a co-solvent, of thiolate of the precious metal, the composition containing 3–22% by weight of the precious metal as the thiolate, and the co-solvent, resin and thiolate being such that as the composition on the substrate dries and is progressively heated in firing, the water evaporates off to leave a homogeneous composition of the resin and thiolate in the co-solvent, then the co-solvent evaporates off to leave a homogeneous composition of the thiolate in the resin, and then the thiolate decomposes to the precious metal while the resin volatilizes.

2. A method according to claim 1, wherein the composition contains 5–85% by weight of water.

3. A method according to claim 1, wherein the composition contains 40–55% by weight of water.

4. A method of claim 1, wherein the precious metal comprises gold.

5. method according to claim 4 wherein the thiolate is a gold compound of the formula Au—S—R—H or Au—S—R—X or a salt of either, in which:

X represents a nitro group or a group of the formula —COOH, —SO$_2$OH, —OH, —CONH$_2$—NH$_2$, or —O—P(O)(OH)$_2$, any of whose hydrogen atoms are optionally substituted and R represents a divalent organic group.

6. A method according to claim 5, wherein the gold compound of formula Au—S—R—H or Au—S—R—X is such that H—R—S—H or H—S—R—X represents:
N-(2-mercaptopropionyl)glycine;
N-(3-mercaptopropionyl)glycine;
N-(2-mercaptoacetyl)glycine;
2-mercaptoacetyl-L-histidine;
3-mercaptopropionyl-L-histidine;
L-cysteine;
acetylcysteine; or
glutathione.

7. A method according to claim 1, wherein the composition contains 8–12% by weight of the precious metal as the thiolate.

8. A method according to claim 1 wherein the resin comprises polyvinyl pyrrolidine, polymethacrylic or polycellulose ether resin, the majority of which volatilizes in the range of 200°–550° C.

9. A method according to claim 1 wherein the composition contains 5–45% by weight of the resin.

10. A method according to claim 1, wherein the co-solvent has a boiling point between 100°–220° C.

11. A method according to claim 1 wherein the co-solvent comprises water-miscible alcohol, ester or ether.

12. A method according to claim 11, wherein the alcohol comprises 1,2-propanediol or 1,3-propanediol.

13. A method according to claim 1 wherein the composition contains 5–45% by weight of the co-solvent.

14. A method according to claim 1, wherein the composition contains in addition precious metal powder or insoluble precious metal compound to produce a burnished film on firing and then burnishing.

15. A method according to claim 1, wherein the composition contains in addition an insoluble matting agent to produce a self-burnished film on firing.

16. A method according to claim 1 wherein the substrate on which firing occurs is ceramic or glass.

17. A method according to claim 1 wherein the firing is at 460°–900° C.

18. A method of forming a film of precious metal, which is one or more of platinum, palladium, gold and silver, on a transfer substrate to prepare a transfer, by applying a homogeneous composition to the transfer substrate and drying the applied composition, said composition comprising polymeric resin and a solution, in water and a co-solvent, of thiolate of the precious metal, the composition containing 3–22% by weight of the precious metal as the thiolate, and the co-solvent, resin and thiolate being such that as the composition on a substrate dries and is progressively heated in firing, the water evaporates off to leave a homogeneous composition of the resin and thiolate in the co-solvent, then the co-solvent evaporates off to leave a homogeneous composition of the thiolate in the resin, and then the thiolate decomposes to the precious metal while the resin volatilizes.

* * * * *